United States Patent [19]

Zollner et al.

[11] 4,428,377
[45] Jan. 31, 1984

[54] METHOD FOR THE ELECTRICAL STIMULATION OF THE AUDITORY NERVE AND MULTICHANNEL HEARING PROSTHESIS FOR CARRYING OUT THE METHOD

[75] Inventors: Manfred Zollner; Christian Hoffmann, both of Munich; Eberhard Zwicker, Icking, all of Fed. Rep. of Germany

[73] Assignee: Siemens Aktiengesellschaft, Berlin & Munich, Fed. Rep. of Germany

[21] Appl. No.: 240,129

[22] Filed: Mar. 3, 1981

[30] Foreign Application Priority Data

Mar. 6, 1980 [DE] Fed. Rep. of Germany ....... 3008677

[51] Int. Cl.³ .............................................. A61N 1/36
[52] U.S. Cl. ............................ 128/419 R; 179/107 R
[58] Field of Search ................................ 128/784–786, 128/789, 419 R, 421; 179/107 R, 107 PC, 107 BC, 107 E, 107 FD

[56] References Cited

U.S. PATENT DOCUMENTS 4,207,441 6/1980 Ricard et al. .................... 179/107 R
4,284,856 8/1981 Hochmair et al. ............ 179/107 BC

FOREIGN PATENT DOCUMENTS 2823798 9/1979 Fed. Rep. of Germany ...... 128/784
2016276 9/1979 United Kingdom ............ 128/419 R

OTHER PUBLICATIONS

Tushar R. Gheewala et al, "A CMOS Implantable Multielectrode Auditory Simulator for the Deaf", *IEEE Journal of Solid-State Circuits*, vol. SC-10, No. 6, Dec. 1975, pp. 472–479.
Hochmair et al, "An 8–Channel . . . Prostheses", IEEE Trans. BME, vol. BME-27, No. 1, Jan. 1980, pp. 44–50.

*Primary Examiner*—Lee S. Cohen
*Attorney, Agent, or Firm*—Hill, Van Santen, Steadman & Simpson

[57] ABSTRACT

In the exemplary embodiments, the sound signals are converted into electrical signals, which are wirelessly transmitted to an implanted receiver, and from the latter, electric stimuli in electrode channels are brought to act on the auditory nerve. The transmission proceeds in the time division multiplex technique in such a manner that the electrical signals are subjected to a pulse modulation and are transmitted in an HF-channel. Thus, the receiver can be reduced with regard to the volume of its construction as well as with regard to its energy requirement. The disclosed method and hearing prostheses for its realization are particularly suited for attending to the needs of the extremely hard of hearing.

4 Claims, 6 Drawing Figures

METHOD FOR THE ELECTRICAL STIMULATION OF THE AUDITORY NERVE AND MULTICHANNEL HEARING PROSTHESIS FOR CARRYING OUT THE METHOD

BACKGROUND OF THE INVENTION

The invention relates to methods for the electrical stimulation of the auditory nerve, and to multichannel hearing prosthesis for carrying out the method. Such methods and prostheses are e.g. known from IEEE Journal of Solid-State Circuits, Vol. SC-10, No. 6, December 1975, pages 472 through 479.

The advancing miniaturization of electronic circuits has led to the manufacture of small stimulation current transmitters which can be implanted in the body for the electric stimulation of nerves and muscles. In addition to serving the function of the stimulation of the heart muscles (heart pacemakers), etc., circuits have also become known which are suitable for stimulation of the auditory nerves. The single channel and multichannel electrode systems are so constructed that they can deliver small stimulation currents. However, they can only be employed for their function as a hearing prosthesis for deaf individuals if the inner ear is, indeed, non-functional, but if the auditory nerve, including higher processing locations for information transmission and information processing, is still intact. In the case of deaf individuals with such impairments, a small receiver can be implanted in the mastoid. Stimulation currents can then be transmitted from the implant via an electrode bundle. The signals are generated, in a portion of the apparatus worn outside the body, from the sound events which are to be conveyed to the wearer of the apparatus, and are transmitted wirelessly via a small transmitter to the implanted receiver in order to avoid an electrically conductive connection through the skin and the related risks of an infection.

The invention proceeds from the assumption that there are per se no significant restrictions regarding construction and size for the portion of the apparatus worn outside the body, i.e., the converter of the sound events into transmittable signals, and for the transmitter, whereas, for the implanted portion, one must proceed from specific constraints such as, for example:

1. The receiver is to possess a small volume (maximally 2 cm$^3$), so that the electrodes can remain short. Long electrode wires result in electric (cross-talk) and mechanical (wire breakage during movement) problems.

2. At least ten to twenty electrodes (according to the application up to twenty-four) are to be capable of being provided, which, in the range of frequencies of between 100 and 5000 Hz, can deliver stimulation currents of at least ten microampers (10 μA), whereby the form of the signals is to be freely selectable within wide boundaries, in order that, following completed implantation, the optimum stimulation current form can be found and adjusted with the patient in experiments.

The internal resistance of the circuit should be as high as possible in order that the current is impressed at the transmission points of the electrodes (electrode tips). However, simultaneously, with regard to electrolysis, the voltage cannot be permitted to become excessively high in order to avoid a damage to the surrounding tissue. If necessary, a current source with voltage limitation would have to be provided for this purpose.

3. The separation of the present channels is to amount to at least thirty decibels (30 dB); i.e., if a stimulation current $J_i$ is generated at an electrode, in the interest of high channel separation, the current brought about by $J_i$ at another electrode should be less than $J_i/32$. The fraction with the denominator thirty-two results from the 30 dB. A value which is greater would further improve the channel separation; i.e., reduce the cross-talk; a value which is smaller would reduce the channel separation to low values.

Moreover, the implanted materials must be compatible with the tissue. The materials cannot be permitted to change even after years of implantation.

SUMMARY OF THE INVENTION

The object underlying the invention, in the case of a prosthesis such as described in the preceding section resides in reducing the outlay regarding space and energy requirements and increasing the performance reliability.

If various independent signals are to be transmitted via a communications channel (designated in the following as the HF-channel), as a rule, one employs the multiplex technique. In the case of frequency-division multiplex, the low-frequency information (of the AF-channels) is modulated onto various high frequency (HF) carriers. High frequency signals in different bands result thereby which must be separated again in the receiver, for example, by means of band-pass filters. For a good separation of the channels, either filters with a steep drop in response outside the pass band or a very broad transmission band are necessary. However, both lead to a construction which, given present-day technology, is counter to the above-cited constraints.

According to the invention, therefore, the transmission of the signals is carried out in time division multiplex technique, in which a number n of AF channels are successively sampled (or scanned) from channel number 1 to channel number n. After the n$^{th}$ channel, again the first channel is sampled, etc. The sampling values are successively transmitted via an HF-channel in the frequency range of around 100 to 500 kilohertz, in particular, 240 kHz. A 5 kHz AF-oscillation, according to the sampling theorem, would have to be sampled at least twice; thus, every T=100 μs. If a total of twenty-four channels are to be transmitted, there remains, for the sampling value of each individual AF-channel, only one time span.

$$\Delta t = 100 \ \mu s/24 = 4.2 \ \mu s.$$

In the receiver, the individual transmitted AF-channels can then again be separated by means of synchronously controlled switches (demultiplexers). For good separation of the channels, a short switching time (less than one microsecond) is desirable. After the switches, holding capacitors ensure "charge storage" for the time between two sampling values.

In order to connect the AF-signals with the HF-channel, preference is to be given to pulse amplitude modulation (PAM) as compared with pulse code modulation (PCM). The last-cited PCM method is, indeed, less sensitive to attenuations in the transmission path. However, during the coding and during the decoding, it requires a greater outlay. Given the present state of technology, however, this leads to difficulties with regard to requirements of space and data flow. The latter is apparent in that, given a specified space in the case of PCM, fewer channels, or a smaller band width, or a smaller dynamic range can be transmitted. Moreover, the reliability of the apparatus decreases because the number of required components is greater. In addition, in the case of PAM-demodulation, a voltage-limited current impression is provided without additional elements.

For the construction of the inventive implantable receiver, commercial integrated components can be employed. CMOS chips have proven expedient which are cemented on 12×12 mm² ceramic plates. Several of these ceramic plates (substrates) can be arranged above one another in sandwich construction. A multilayer thick laminar module, known per se, connects the highly integrated chips with one another. As assembly technique, the ultrasonic wire bond method can be employed. Lines which can connect the substrates with one another are designed in the form of small metal comb-like conductor arrays. In the case of the selected technology, it is possible to manufacture a 24-channel receiver in the size of 12×12×5 mm³ (without housing).

A reduction of the receiver can be achieved if monolithic, integrated components are employed. However, on the other hand, in particular instances, an additional reduction in the volume of the receiver can be realized through omission of individual substrates, in case e.g. the transmission of only eight or sixteen channels should prove satisfactory for speech intelligibility. On the other hand, an increase in the number of channels can be achieved through addition of substrates and enlargement of the volume. However, the transmission band width is thus reduced, because the sampling would have to proceed in larger time intervals.

On the other hand, the housing exhibits connections for the two receiving induction coils, which receive the signals transmitted externally to the conversion apparatus via two transmitting coils. Moreover, connections of the electrodes proceed out of the housing. The latter are combined into a bundle in a manner known per se. Jointly with the housing the bundle of electrodes is coated with a tissue compatible material, for example, a plastic, such as silastic.

The dimensions of the electrodes result from a compromise between current density and space required for the transmission. A bundle of electrodes with approximately twenty individual electrodes should have an overall diameter less than the diameter of the auditory nerve. For the individual electrodes, thus a diameter of approximately one hundred microns (100 μm) enters into consideration. This is a value which cannot by any means be permitted to be randomly fallen short of, because a stimulation current of up to ten microampers (10 μA) must be transmitted which already yields a current density of 100 mA/cm². If such high current densities are generated over a long time, the result can be a destruction of the tissue resting against the electrode. In addition to the stimulation current density, also the stimulation voltage must be taken into consideration. Depending upon the electrode metal and stimulation frequency, an electrolysis can occur already at one-half to one volt (0.5 to 1 V), which likewise leads to the destruction of the tissue. The electrodes are so designed that they strike the auditory nerve in the inner auditory passage in a manner known per se.

The band width in each AF-channel amounts to five kilohertz (5 kHz). This value is determined by the sampling in the 100 μs-interval. The band width of 5 kHz has proven optimum in the case of earlier investigations (e.g. German Patent Application 29 08 999.4), although also bandwidths of 100 Hz to 10 kHz are applicable, depending upon whether a smaller or greater outlay is desired. The channel separation is greater than 40 dB between adjacent channels (measured values on a prototype). Between further removed channels, even values of more than 50 dB were attained. The harmonic distortion attenuations were measured, in the case of transmissions of a one kilohertz (1 kHz) sine tone, in the range of zero to five kilohertz (0 to 5 kHz). Depending upon modulation; i.e., depending upon the transmitted voltage amplitude, values resulted of between 30 to 40 dB. The signal-to-noise ratio, measured in a non-evaluated fashion; i.e., linearly, amounts to approximately 60 dB in the frequency range of 2 Hz to 5.6 kHz.

Further advantages and details of the invention shall be explained in greater detail in the following on the basis of the exemplary embodiments illustrated in the Figures of the accompanying drawing sheet; and other objects, features and advantages will be apparent from this detailed disclosure and from the appended claims.

DETAILED DESCRIPTION

Figure 1:
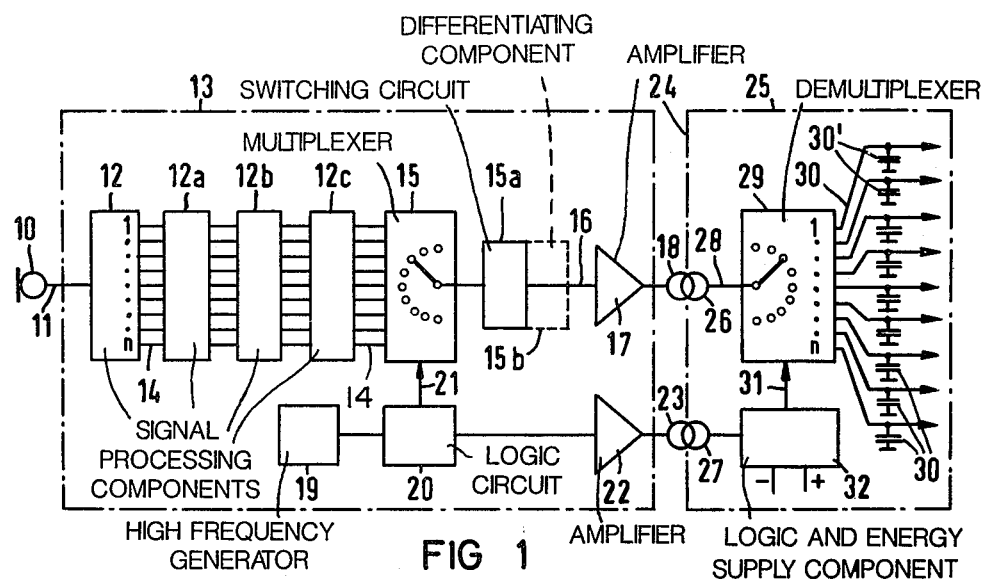
In FIG. 1, in a basic block circuit diagram, an embodiment of the inventive construction is illustrated; and In FIGS. 2 through 6, in diagrams, the plotting of the sampling values of the PAM in chronological progression is illustrated.

In FIG. 1, 10 designates a microphone which is connected via a line 11 with a signal processing installation 12, which forms a portion of the transmitter part 13 of the inventive prosthesis to be worn outside on the body.

In the installation, the signal arriving via 11 is first separated e.g. into individual frequency bands by processing component 12 (e.g. same band widths and mean frequencies as in German patent application No. 29 08 999.4), and then e.g. matched by component 12a in its dynamic range to the dynamic range of the nerve fibers which lie in the immediate vicinity of the respective electrode tip. The allocation of the band-pass filters, determining the frequency bands, to the individual AF-channels; i.e., to the individual electrodes, can, following completed implantation, be carried out individually for each patient in the transmitter in the crossbar distributor component 12c (matching to the patient). If necessary, it is also possible to connect, between the band-pass filter (12a) and crossbar (12c), a pulse shaper (12b), with which the output signals of the band-pass filters are variable according to the requirements of the patient. Since, only in collaboration with the patient can the waveform of the signal, etc., which is optimum for him, be ascertained, an implanted receiver, whose data, as a rule, can no longer be changed, must be so universally constructed that it can deliver a plurality of signal waveforms (i.e., stimulation current waveforms). The proposed circuit ideally satisfies this demand on account of its high bandwidth of 0 to 5 kHz. The processed signals are, as indicated with the lines 14, supplied to a multiplexer 15, which then conducts, in chronological sequence, a sampling of the channels supplied via 14, so that, via a line 16 and an amplifier 17, the signal to be transmitted is supplied to a transmitting coil 18. For controlling the multiplexer 15, high frequency generator 19 is provided in the part 13 which effects, via a logic circuit 20, the control of the multiplexer 15, as indicated by an arrow 21. On the other hand, a forwarding to an amplifier 22 takes place, to which an induction coil 23 is connected. As indicated by a broken line 24, both coils 18 and 23 rest externally against the body of the wearer of the prosthesis who is implanted with a receiver referenced with 25. Within the body, there is disposed, opposite the coils 18 and 23, a coil 26 and 27, respectively, so that the electric signals arriving from the coil 18 are transmitted, on the one hand, and the high frequency signal of generator 19 is transmitted, on the other hand. The signals of coil 26 are supplied via a line 28 to a demultiplexer 29 in which, synchronously with the sampling in 15, a sampling takes place which, in the manner indicated by 1 . . . n, delivers signals to electrodes indicated by the arrow symbols associated with lines 30. The synchronization proceeds, as indicated by a line 31, via the high frequency arriving from coil 27, which is processed in a circuit logic component 32, so that the synchronization takes place, on the one hand, and—as indicated by the outputs designated plus and minus of component 32—the supply of the receiver 25 with direct current energy from the transmitted high frequency takes place, on the other hand.

The described PAM circuit comes quite close to the demands for current impression with voltage limitation: under the assumption that the holding capacitors at 30', which are connected between the electrode-leads indicated by arrows 30 (FIG. 1) and ground potential, are charged with each sampling value and, in the time between two sampling values, are largely discharged. An impression of the mean electrode current results $$\bar{I}_i = \frac{1}{\Delta t} \int_0^{\Delta t} I_i(t) dt.$$

For low-impedance load resistances (tissue resistances), a higher current flows for a short time, and, for high-impedance load resistances, a lower current flows for a longer time. However, the current mean value remains virtually the same, as long as the load resistance does not exceed a specific resistance. However, this is not to be expected in the case of an apparatus according to the invention, because metal electrodes of the indicated diameter yield low resistances. A limitation of the voltage results automatically by the operating voltage of the receiver of approximately plus and minus four volts (±4 V), which is rather low with respect to a small power consumption. A possibly necessary additional limitation of the operating voltage, in order to avoid electrolysis, can be readily installed, for example in the form of limiter diodes which limit the voltage at the coil 26.

Figure 2:
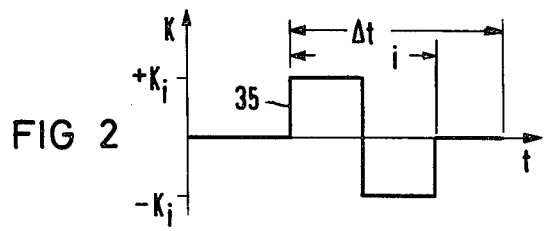

In FIG. 2, the value K of the sampling of the PAM, which fluctuates between $K_i$ and $-K_i$, is plotted on the abscissa relative to the time t, whereby it is shown that, in order to achieve d.c. voltage-free transmission in the first third of the time $\Delta t$, which is available for the transmission of the channel, the sampling value $K_i$ is transmitted. In the second third of the time slot, the negative sampling value; i.e., $-K_i$, is transmitted. Without this measure, the PAM signal would not be d.c. voltage-free, and since the transmitter (cf. 18, 26, FIG. 1) cannot transmit any d.c. voltages, a higher outlay would have to be expended during the decoding in order to compensate resulting transmission errors. In the last third of the time slot, no voltage is then transmitted any longer, so that during this time the multiplexer can switch over to the next channel. This measure enlarges the channel separation.

In the receiver 25 the first third of the multiplex time slot for each channel is sampled. With this sampling value, via the demultiplexer switch 29, a holding capacitor 30' is then charged (FIG. 1). The discharge of this capacitor via the load resistance $R_L$, which is formed by the tissue bordering on the electrode, then corresponds, by way of approximation, to the desired current impression of $\bar{I}_i$, if the value of the capacitor C is greater than $\Delta t/R_L$. The value of C of approximately five hundred picofarads (500 pF) has proven favorable.

However, the sampling values can also be transmitted with another arrangement of the time periods. In comparison with the progression of curve 35 of the sampling values according to FIG. 2, curve 36 of FIG. 3 yields a progression in which first the positive sampling proceeds, then a voltage-free section 37, and only following this does the negative portion 38 occur, which is finally again followed by a voltage-free part 39.

Figures 3, 4:
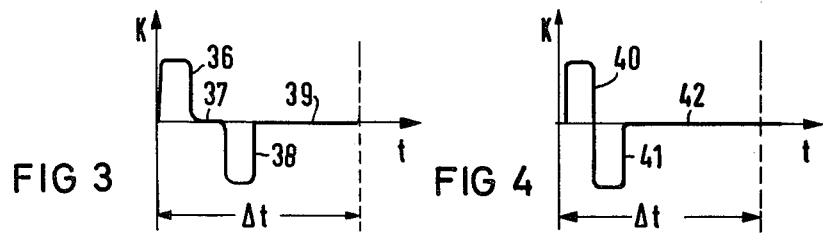

On the other hand, however, it is also possible, as is indicated in FIG. 4, to place the positive portion 40 of the sampling and the negative portion 41 closely together on the first portion of the sampling in order to obtain a longer voltage-free portion 42 separating the channels.

Figures 5, 6:
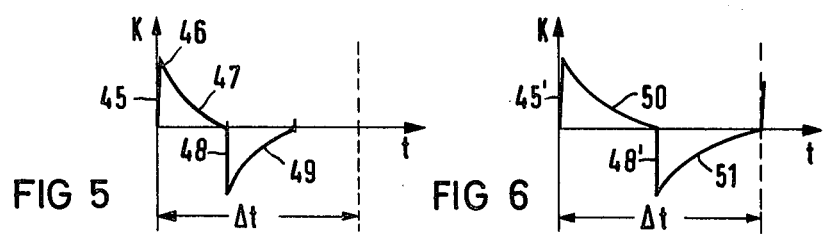

Another variation can be achieved through differentiation of the sampling values, so that the progression illustrated in FIGS. 5 and 6 is obtained. As is indicated in broken lines in FIG. 1, the differentiation can proceed in a differentiation member 15b. The progression of the sampling values to be transmitted then exhibits a steep rise 45 and a peak 46. This is followed by a somewhat more gradual drop 47 which, with commencement of the negative portion of the sampling value, passes into a steep drop 48, which then passes into an increase 49 whose rate of change (slope) largely corresponds to the rate of change in the drop 47.

In the manner illustrated in FIG. 6, the rise 45', indeed, corresponds to that referenced in FIG. 5 with 45; likewise, the steep drop referenced with 48' corresponds to 48 in FIG. 5. Only the drop 50 and the rise 51 are more gradual than those in FIG. 5.

According to FIG. 5 as well as according to FIG. 6, through the differentiation, a signal is attained which is free of d.c. current components. For generating differentiated signals in component 15b, a circuit 15a can also be so designed that, instead of ⅓ of the time slot consisting of $+K_i$ and ⅓ of $-K_i$, etc., only a switching-on and-off of the same signal occurs, respectively; i.e., only $+K_i$ or only $-K_i$ occur. A signal corresponding to FIG. 5 can already thus be obtained e.g. from the positive portion of the curve 35 (portion of the curve 35 of FIG. 2 in the range of $+K_i$ lying above the time axis t).

It will be apparent that many modifications and variations may be effected without departing from the scope of the novel concepts and teachings of the present invention.

We claim as our invention:
1. A hearing prosthesis for the electric stimulation of the auditory nerve, comprising
(a) an implantable receiver means having multiple electrode output means for the supply of electric stimulation to the auditory nerve and having receiving coil means for receiving transmitted stimulation signals,
(b) wireless transcutaneous signal transmission means for transmitting stimulation signals to the receiving coil means via an inductive coupling with the receiving coil means of said implantable receiver means for effecting the electric stimulation of the auditory nerve via the multiple electrode output means of the implantable receiver means, (c) a signal processing installation including means for receiving an acoustic signal and having a plurality of low frequency output channels for supplying respective frequency bands of the acoustic signal, (d) said signal processing installation having high frequency generator means for controlling the sampling of the respective output channels, (e) said signal processing installation having pulse amplitude modulated transmission means controlled by said high frequency generator means and coupled with said low frequency output channels and with said wireless transcutaneous signal transmission means for sequentially sampling the output channels and transmitting signal samples to the wireless transcutaneous signal transmission means from the respective output channels in pulse amplitude modulated fashion and with a pulse envelope of alternating polarity, and (f) said implantable receiver means having demultiplexer means coupled with said receiving coil means and with said multiple electrode output means for supplying electric stimulation signals in accordance with respective received signal samples to the respective electrode output means in sequence.

2. A hearing prosthesis according to claim 1, with said high frequency generator means having an amplifier coupled with said wireless transcutaneous signal transmission means for the transmission of an amplified high frequency signal to said receiving coil means separately from said signal samples, and said implantable receiver means having operating energy supply means coupled with said receiving coil means for converting the received amplified high frequency signal into operating electric energy for the implantable receiver means.

3. A hearing prosthesis according to claim 2, with said demultiplexer means having a control input coupled with said receiving coil means for receiving said high frequency signal to control demultiplexing operation, and having respective demultiplexer outputs including respective individual signal sample storage capacitor means for providing electric stimulation signals to the respective electrode output means.

4. A hearing prosthesis according to claim 1, with said implantable receiver means comprising individual capacitance means connected with the respective electrode output means and connected with respective outputs of said demultiplexer means for sequentially receiving respective demultiplexed signal samples therefrom.

* * * * *